(12) United States Patent
Huang et al.

(10) Patent No.: US 6,899,992 B2
(45) Date of Patent: May 31, 2005

(54) POLYMERIZABLE COMPOUNDS WITH QUADRUPLE HYDROGEN BOND FORMING GROUPS

(75) Inventors: Jianbing Huang, Trumball, CT (US); Shashikant Saraiya, Parlin, NJ (US); Xing-Fu Zhong, Wallington, NJ (US)

(73) Assignee: Kodak Polychrome Graphics LLC, Norwalk, CT (US)

( * ) Notice: Subject to any disclaimer, the term of this patent is extended or adjusted under 35 U.S.C. 154(b) by 154 days.

(21) Appl. No.: 10/290,623

(22) Filed: Nov. 8, 2002

(65) Prior Publication Data

US 2004/0091812 A1 May 13, 2004

(51) Int. Cl.$^7$ ................................................ G03F 7/004
(52) U.S. Cl. ................................ 430/270.1; 430/271.1; 430/273.1; 430/300; 430/320; 430/322; 430/326; 528/423
(58) Field of Search .......................... 430/270.1, 271.1, 430/273.1, 300, 320, 322, 326; 528/423

(56) References Cited

U.S. PATENT DOCUMENTS

| | | | |
|---|---|---|---|
| 6,320,018 B1 | 11/2001 | Sijbesma et al. | |
| 6,506,536 B2 | 1/2003 | Pappas et al. | 430/270.1 |
| 2003/0118939 A1 * | 6/2003 | Munnelly et al. | 430/273.1 |
| 2004/0034190 A1 * | 2/2004 | Janssen et al. | 528/423 |

FOREIGN PATENT DOCUMENTS

| | | |
|---|---|---|
| EP | 1031589 | 8/2000 |
| EP | 1213309 | 6/2002 |
| WO | WO 98/14504 | 4/1998 |
| WO | 01/07396 | 2/2001 |
| WO | 02/053626 | 7/2002 |
| WO | 02/053627 | 7/2002 |

OTHER PUBLICATIONS

Kilian et al, "Synthesis and Characterization of Responsive Macromolecules," vol. 43, pp. 916–917 (2002).

Ohsaki et al, "Supramolecular Acid/Base Catalysis via Multiple Hydrogen Bonding Interaction," pp. 1690–1691 (2002).

Folmer et al, "Supramolecular Polymer Materials: Chain Extension of Telechelic Polymers Using a Reactive Hydrogen–Bonding Synthon," Advanced Materials, vol. 12, pp. 875–878 (2000).

Hirschberg et al., "Supramolecular Polymers from Linear Telechelic Siloxanes with Quadruple–Hydrogen–Bonded Units," Macromolecules, vol. 32, pp. 2696–2705 (1999).

* cited by examiner

Primary Examiner—Yvette C. Thornton
(74) Attorney, Agent, or Firm—RatnerPrestia

(57) ABSTRACT

QHB-Modified free radical polymerizable compounds and free radical polymerizable compositions that comprise these compounds are disclosed. A QBH-modified free radical polymerizable compound has at least one moiety that comprises at least one free radical polymerizable group; a supporting backbone, and at least one and preferably at least two moieties capable of forming four or more, typically four, hydrogen bonds with similar or complementary units on other molecules or portions of molecules. Free radical polymerizable compositions that contain these compounds may be used in any of the well-known applications for free radical polymerizable compositions. They are especially useful for the formation of imageable elements useful as lithographic printing plate precursors.

70 Claims, No Drawings

POLYMERIZABLE COMPOUNDS WITH QUADRUPLE HYDROGEN BOND FORMING GROUPS

FIELD OF THE INVENTION

This invention relates to polymerizable compounds and to polymerizable compositions that comprise the polymerizable compounds. In particular, this invention relates to free radical polymerizable compounds containing quadruple hydrogen bond forming groups and to their use in imageable elements.

BACKGROUND OF THE INVENTION

Polymerizable compositions that comprise a free radical polymerizable compound, a binder, and an initiator system are well known. The free radical polymerizable compound, or monomer, comprises at least one ethylenically unsaturated group that undergoes free radical initiated polymerization. Monomers are typically multifunctional, i.e., they comprise more than one ethylenically unsaturated, free radical polymerizable group.

For efficient polymerization, the monomer or mixture of monomers used in the composition is typically a liquid at room temperature. However, because liquid monomers are difficult to use in commercial products, a film forming polymer, known as the binder, is added to the composition so that the composition can be coated and handled as a dry film.

Despite the many advantages of these polymerizable compositions, it would be advantageous to have polymerizable compositions that form dry films but do not require a binder so that the binder can be omitted from the composition. Thus, a need exists for polymerizable compounds that form dry films at ambient temperature and undergo efficient polymerization when polymerization is initiated by a free radical generating system.

SUMMARY OF THE INVENTION

In one aspect, the invention is QHB-modified free radical polymerizable compound. A QHB-modified free radical polymerizable compound has the general structure:

$(P)_m B(Q)_n$ in which:
Q is a moiety that comprises a QHB unit;
P is a moiety that comprises at least one free radical polymerizable group;
B is a supporting backbone;
$m \geq 1$, and
$n \geq 1$, preferably $n \geq 2$.

P typically has 1 to 5 free radical polymerizable groups, preferably 2 or 3 free radical polymerizable groups.

In another aspect, the invention is a free radical polymerizable composition comprising the QHB-modified polymerizable compound and a free radical generating system. In another aspect, the invention is an imageable element useful as a lithographic printing plate precursor. The imageable element comprises a layer of the free radical polymerizable composition (an imageable layer) on a substrate. In another aspect, the invention is a method for forming an image by imaging and developing the lithographic printing plate precursor.

DETAILED DESCRIPTION OF THE INVENTION

Unless the context indicates otherwise, in the specification and claims, the terms QHB-modified free radical polymerizable compound, free radical polymerizable monomer, photothermal conversion material, and similar terms include mixtures of such materials. Unless otherwise specified, all percentages are percentages by weight. "QHB-modified" refers to a molecule or a portion of a molecule that comprises a QHB (quadruple hydrogen bonding) unit that is capable of forming four or more, typically four, hydrogen bonds with similar or complementary units on other molecules or portions of molecules.

QHB-Modified Polymerizable Compounds

The QHB-modified polymerizable compounds have the structure $(P)_m B(Q)_n$, in which Q is a moiety that comprises at least one QHB unit; P is a moiety that comprises at least one free radical polymerizable group; and B is a supporting backbone.

A QHB (quadruple hydrogen bonding) unit is capable of forming four or more, typically four, hydrogen bonds with similar or complementary units on other molecules or portions of molecules. Polymeric molecules that, in pairs, form at least four hydrogen bonds with one another are disclosed in Sijbesma, U.S. Pat. No. 6,320,018, and Pappas, U.S. Pat. Pub. 2002/0150833 A1, both of which are incorporated herein by reference.

QHB units preferably have an essentially flat, rigid structure. In particular, the unit preferably contains one or more flat six-membered rings. Preferably, the QHB units have two successive donors, followed by two acceptors. Typical QHB units include, for example:

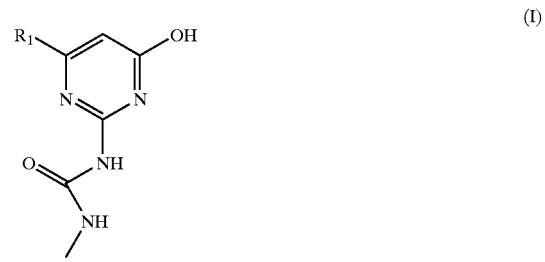

(I)

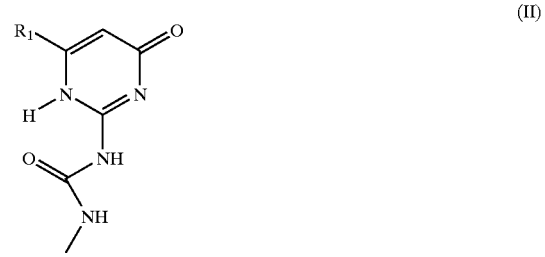

(II)

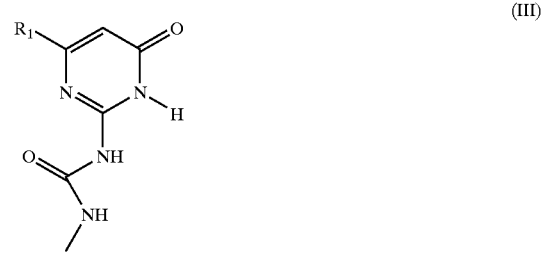

(III)

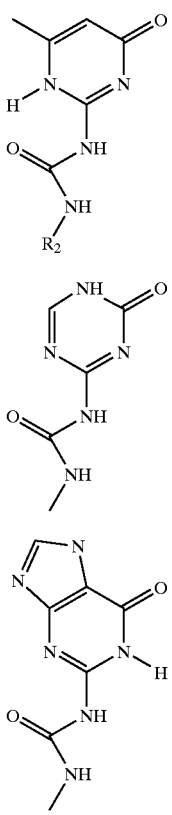

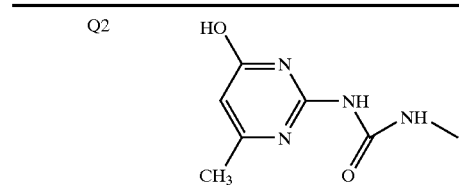

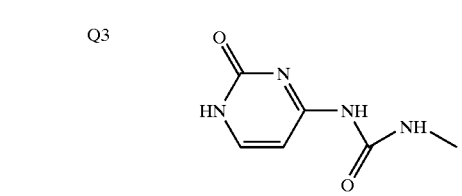

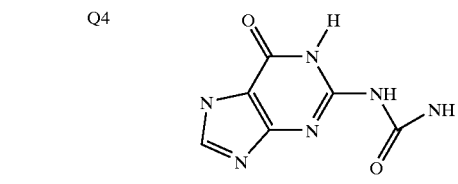

where I, II, and III are tautomeric forms of isocytocine, and $R_1$ is hydrogen or a hydrocarbon group with or without heteroatoms, typically an alkyl group of 1 to 10 carbon atoms, more typically methyl; and $R_2$ is a residue from an isocyanate, which may further comprise one or more moieties that comprises at least one free radical polymerizable group.

In one embodiment, the QHB units comprise isocytocine units (isocytocine moieties). A QHB-modified compound can be prepared by reaction of, for example, a 2-amino-4-hydroxy-6-alkyl pyrimidine, such as 2-amino-4-hydroxy-6-methyl pyrimidine (also called methyl isocytocine), with a polyisocyanate to produce an isocytocine/isocyanate adduct, called a quadruple hydrogen bonding entity (QHBE).

Examples of Q, the moiety that comprises a QHB unit, are:

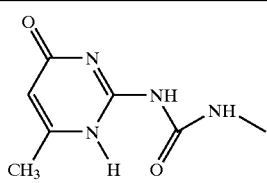

Any polyisocyanate may be used to prepare the QHBE. Suitable diisocyanates include, for example, isophorone diisocyanate, methylene-bis-phenyl diisocyanate (MDI), 2,4-toluene diisocyanate, 2,6-toluene diisocyanate, hexamethylene diisocyanate (HDI), m-tetramethylxylene diisocyanate, 1,5-napthalene diisocyanate, trans-1,4-cyclohexane diisocyanate, and norbornane diisocyanate. Other polyisocyanates include dimers, trimers, and higher oligomers of these diisocyanates, adducts of these diisocyanates with diols and other polyols, and mixtures of these polyisocyanates. A preferred diisocyanate is the trimer of hexamethylene diisocyanate, which has three free isocyanate groups attached by hexamethylene groups to a ring formed by trimerization of three isocyanate groups.

When the polyisocyanate is a diisocyanate, reaction of one mole of the isocytocine with one mole of the diisocyanate produces mainly a QHBE, that has a free isocyanate group, which can undergo further reaction to produce the QHB-modified free radical polymerizable compound. When the polyisocyanate has more than two isocyanate groups, more than one mole of the isocytocine may react with one mole of polyisocyanate to produce a QHBE that has more than one QHB group. The resulting QHBE may also have more than one free isocyanate group, so that further reaction produces a QHB-modified free radical polymerizable compound that comprises more than one moiety that comprises at least one free radical polymerizable group. That is, when the polyisocyanate is a diisocyanate of the general structure $Y(NCO)_2$, the QHBE has the general structure:

Q-Y—NCO.

When the polyisocyanate is hexamethylene diisocyanate, for example, Y is —$(CH_2)_6$—.

When the polyisocyanate has the general structure $Y(NCO)_p$, the QHBE has the general structure:

$(Q)_{p-q}$-Y—$(NCO)_q$ in which q is an integer of 1 or greater and p is an integer of 2 or greater. For a polyisocyanate that has thee isocyanate groups, for example, p is 3.

P, the moiety that comprises at least one free radical polymerizable group, may be derived from a compound that has least one free radical polymerizable group and at least one isocyanate reactive group, such as hydroxyl, amino, mercapto, carboxyl, etc. Typical free radical polymerizable compounds have one or more groups that contain C=CH$_2$ functionality, typically the —CH=CH$_2$ or —C(CH$_3$)=CH$_2$ functionality, such as acrylate, methacrylate, stryryl, vinyl ether, etc. Examples of suitable compounds include hydroxyalkyl esters of acrylic acid or methacrylic acid, such as, 2-hydroxyethyl acrylate, 2-hydroxyethyl methacrylate, 3-hydroxypropyl acrylate, 3-hydroxypropyl methacrylate, 4-hydroxybutyl acrylate, 4-hydroxybutyl methacrylate, 6-hydroxylhexyl acrylate, 6-hydroxyhexyl methacrylate, neopentyl glycol monoacrylate, neopentyl glycol monomethacrylate, polyethylene glycol monoacrylate, polyethylene glycol monomethacrylate, glycerol monoacrylate, glycerol monomethacrylate, glycerol diacrylate, glycerol dimethacrylate, trimethylol propane monoacrylate, trimethylol propane monomethacrylate, trimethylol propane diacrylate, trimethylol propane dimethacrylate, bisphenol A diglycidyl ether diacrylate and oligomers thereof, bisphenol A diglycidyl ether dimethacrylate and oligomers thereof, pentaerythritol diacrylate, pentaerythritol dimethacrylate, pentaerythritol triacrylate, pentaerythritol trimethacrylate, dipentaerythritol monohydroxy pentaacrylate, dipentaerythritol monohydroxy pentamethacrylate, 2-amino ethyl acrylate, 2-amino ethyl methacrylate; hydroxyalkyl vinyl ethers, such as 1,4-butanediol monovinyl ether and pentaerythritol trivinyl ether; styrenes, such as p-hydroxystyrene, p-aminostyrene, and p-hydroxymethylstyrene; aminoalkyl esters and amides of polymerizable unsaturated acids, such as, 2-aminoethyl acrylate, 2-aminoethyl methacrylate, N-(3-aminopropyl) acrylamide, N-(3-aminopropyl)methacrylamide, N-(2-aminoethyl)acrylamide, N-(2-aminoethyl)methacrylamide; metcaptoalkyl esters of polymerizable unsaturated acids, such as 2-mercaptoethyl acrylate, 2-mercaptoethyl methacrylate; carboxyl containing esters of polymerizable unsaturated acids, such as dimethylol propionic acid diacrylate and dimethylol propionic acid dimethacrylate, etc.

Compounds that contain other reactive groups may be used. Other possible precursors for P include, for example, isocyanatoethyl acrylate and isocyanatoethyl methacrylate.

For a QHB-modified free radical polymerizable compound formed from pentaerythritol triacrylate and a polyisocyanate, P has the structure:

—NH—CO—O—CH$_2$—C—(CH$_2$—O—CO—CH=CH$_2$)$_3$.

For a QHB-modified free radical polymerizable compound formed from a polyisocyanate and 2-hydroxyethyl acrylate, P has the structure:

—NH—CO—O—(CH$_2$)$_2$—O—CO—CCH=CH$_2$.

For a QHB-modified free radical polymerizable compound formed from a polyisocyanate and 6-hydroxyhexyl methacrylate, P has the structure:

—NH—CO—O—(CH$_2$)$_6$—O—CO—C(CH$_3$)=CH$_2$.

Other possible structures for P include, for example:

—NH—CO—NH—(CH$_2$)$_2$—O—CO—CCH=CH$_2$,

—NH—CO—O—(CH$_2$)$_2$—O—CH=CH$_2$,

—NH—CO—O-p-(C$_6$H$_4$)—CH=CH$_2$,

—O—CO—C(CH$_3$)=CH$_2$,

—O—CO—CH=CH$_2$, and

—O—CO—NH—(CH$_2$)$_2$—O—CO—CH=CH$_2$.

Other structures for P will be apparent to those skilled in the art.

For the preparation of free radical polymerizable compositions, free radical polymerizable compounds that contain more than one free radical polymerizable group and one isocyanate reactive group, such as pentaerythritol triacrylate, pentaerythritol trimethacrylate, dipentaerythritol monohydroxy pentaacrylate, dipentaerythritol monohydroxy pentamethacrylate, are preferred. When the QHBE has only one unreacted isocyanate group, free radical polymerizable compounds that have more than one isocyanate reactive group are preferred.

Free radical polymerizable compounds that contain more than one isocyanate reactive group, such as pentaerythritol diacrylate, pentaerythritol dimethacrylate, and bisphenol A diglycidyl ether diacrylate, may react with more than one QHBE and produce QHB-modified free radical polymerizable compounds in which the free radical polymerizable group, P, is attached to more than one supporting backbone, B. Such QHB-modified free radical polymerizable compounds are included in the scope of the invention.

B, the supporting backbone, is the group or moiety that connects the Q moiety or moieties with the P moiety or moieties.

For example, when hexamethylene diisocyanate is used as the diisocyanate and 1,4-butanediol as the chain extender, B has the structure:

—(CH$_2$)$_6$—(NHCO—O—(CH$_2$)$_4$—O—CO—NH(CH$_2$)$_6$—)$_s$— in which s is zero or a positive integer, whose value depends on the molar ratio of the ingredients used in preparation of the QHB-modified free radical polymerizable compound. Other examples of B include:

B1
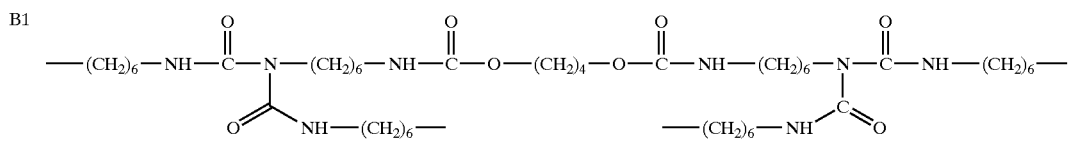

B2
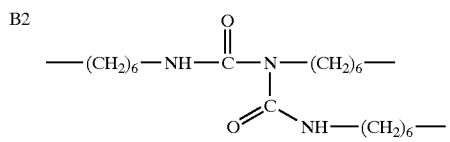

B3 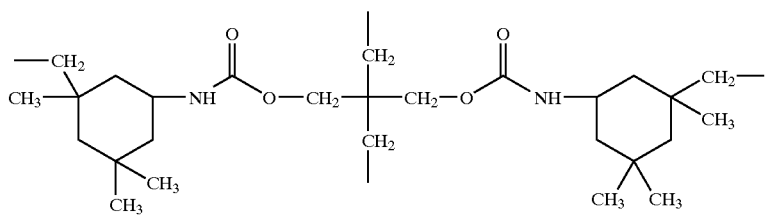

B4 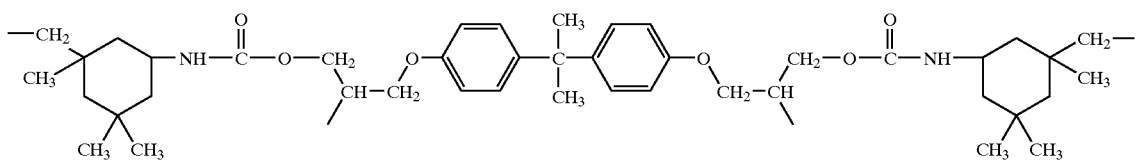

B5 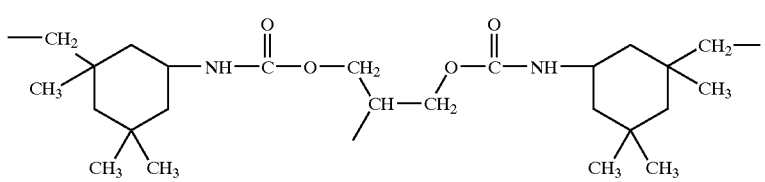

Other possible structures for B will be apparent to those skilled in the art.

The QHBE may also be reacted with a mixture of free radical polymerizable compounds, one or more of which contain one free radical polymerizable group and one or more of which contain more than one free radical polymerizable group. In this manner, the amount of crosslinking in the product produced by polymerization of the QHB-modified free radical polymerizable compound can be controlled.

To prepare the QHB-modified free radical polymerizable compound, the compound, or mixture of compounds, that contains the free radical polymerizable group or groups may be added to the reaction mixture that contains the QHBE and unreacted polyisocyanate. Because unreacted polyisocyanate is present, only part of the compound that contains the free radical polymerizable group or groups reacts with the QHBE to produce the QHB-modified free radical polymerizable compound. The rest of the compound reacts with the unreacted polyisocyanate to produce an adduct that has one or more free isocyanate group. To produce a high molecular weight QHB-modified free radical polymerizable compound, a chain extender, typically a diamine or a diol, such as ethylene glycol or 1,4-butanediol, is usually added.

Alternatively, the QHB-modified free radical polymerizable compound may be prepared by adding a diol to the polyisocyanate to form a polyisocyanate/diol adduct which contains unreacted isocyanate groups. The isocytocine is added and reacts with the unreacted isocyanate groups to form the QHBE. The compound, or mixture of compounds, that contains the free radical polymerizable group or groups is added to the reaction mixture that contains the QHBE. If desired, an end capper, for example an amine or an alcohol that contains only one isocyanate reactive group such as 2-methoxyethanol, is added to react with any remaining free isocyanate groups.

B may be attached to more than one moiety that comprises a QHB unit (Q) and/or more than one moiety that comprise a free radical polymerizable group (P). B preferably has at least 2, more preferably 2, that is, (p-q) is more preferably 2.

Although the preparation of QHB-modified free radical polymerizable compounds has been described with respect to the use of isocyanates to form B, the formation of QHB-modified free radical polymerizable compounds is not so limited. Other reagents can be used to form the QHB-modified free radical polymerizable compounds.

Polymerizable Compositions

The free radical polymerizable compositions comprise the QHB-modified free radical polymerizable compound or a mixture of the QHB-modified free radical polymerizable compounds and a free radical generating system. Other ingredients that are conventional ingredients of free radical polymerizable compositions may also be present. Although polymeric binders may be present in the free radical composition, they are typically unnecessary. The QHB-modified free radical polymerizable compound or a mixture of the QHB-modified free radical polymerizable compounds typically comprises 70 to 95 wt % of the polymerizable composition.

Free Radical Generating System

The free radical generating system can be any single compound or combination of compounds that generate free radicals that initiate the polymerization of the monomer or monomers without excessive termination. Selection of the free radical generating system will depend on the intended use of the free radical polymerizable composition. The free radical generating system may be sensitive to heat and/or to visible, ultraviolet radiation, and/or infrared radiation.

Free radical generating systems sensitive to heat include well known thermal initiators such as persulfates, peroxides such as benzoyl peroxide, and azo compounds, such as azobisisobutyrodinitrile (AIBN; VAZO® 64) and similar compounds (VAZO® 52, VAZO® 67, VAZO® 88, VAZO® 44WSP, VAZO® 56WSP, etc.) Free radical generating systems sensitive to visible and/or ultraviolet radiation are disclosed in "Photoinitiators for Free Radical Initiated Photoimaging Systems," by B. M. Monroe and G. C. Weed, Chem. Rev., 93, 435–448 (1993) and in "Free Radical Polymerization" by K. K. Dietliker, in *Chemistry and Technology of UV and EB Formulation for Coatings, Inks, and Paints*, P. K. T. Oldring, ed, SITA Technology Ltd., London, 1991, Vol. 3, pp. 59–525. Examples include substituted and unsubstituted polynuclear quinones, benzophenone; benzophenone and 4,4'-bis(dimethylamino)benzophenone; benzophenone and 4,4'-bis(diethylamino)benzophenone; 2-hydroxy-2-methyl-1-phenylpropan-1-one; 2,4,6-trimethylbenzolyl-diphenylphosphine oxide; 2,2-dimethoxy-2-phenyl-acetophenone (benzildimethyl ketal; 2-methyl-1-(4-(methylthio)phenyl)-2morpholinopropanone-1; 1-hydroxycyclohexylphenyl ketone; bis(2,6dimethoxybenzolyl)-2,4,4-trimethylpentylphosphine oxide; and combinations thereof. A free radical generating systems sensitive to visible and/or ultraviolet radiation typically comprises about 0.001 wt % to 10.0 wt % of the weight of the free radical polymerizable composition, based on the total weight of the composition.

In one embodiment, especially useful for compositions that will be polymerized using infrared radiation, the free radical generating system comprises a polyhaloalkyl-substituted free radical-producing compound or a mixture of polyhaloalkyl-substituted free radical-producing compounds and carboxylic acid of the formula shown below. Polyhaloalkyl-substituted free radical-producing compounds comprise at least either one polyhalogenated or several monohalogenated or dihalogenated alkyl substituents. The halogenated alkyl group preferably has 1 to 3 carbon atoms. A preferred halogenated alkyl group is the halogenated methyl group. Suitable polyhaloalkyl-substituted compounds include, for example: halo-substituted-s-triazines, such as 2,4,6-tris(trichloromethyl)-s-triazine, 2,4,6-tris(tribromomethyl)-s-triazine; 2-phenyl-4,6-bis(trichloromethyl)-s-triazine, 2-(4-methoxyphenyl)-4,6-bis(trichloromethyl)-s-triazine, 2-(4-chlorophenyl)-4,6-bis(trichloromethyl)-s-triazine, 2-(4-methylthiophenyl)-4,6-bis(trichloromethyl)-s-triazine, and 2,4,6-tris(tribromomethyl)-s-triazine; and other halogenated compounds, such as tribromomethyl phenylsulfone, and 1,2,3,4-tetrabromo-n-butane. In this embodiment, the free radical polymerizable composition typically comprises about 2 to about 15 wt %, preferably about 4 to about 7 wt %, polyhaloalkyl-substituted free radical-producing compound or a mixture of polyhaloalkyl-substituted free radical-producing compounds, based on the total weight of the free radical polymerizable composition.

The absorption properties of the polyhaloalkyl-substituted compound determine the daylight stability of the imageable element. If a high degree of daylight stability is desired, polyhaloalkyl-substituted compounds that do not have significant ultraviolet/visible absorption at >330 nm are preferred.

In this embodiment, the free radical generating system also comprises a carboxylic acid of the following formula:

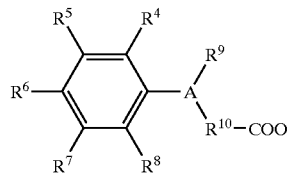

in which:

$R^4$, $R^5$, $R^6$, $R^7$ and $R^8$ are each independently selected from the group consisting of hydrogen, alkyl, aryl, halogen, alkoxy, hydroxyalkyl, carboxy, carboxyalkyl, alkylthio, alkylsulfonyl, sulfonic, alkylsulfonate, dialkylamino, acyl, alkoxycarbonyl, cyano and nitro; or $R^4$ and $R^5$, $R^5$ and $R^6$, $R^6$ and $R^7$, or $R^7$ and $R^8$ together form an aromatic or aliphatic ring;

$R^9$ is selected from the group consisting of hydrogen, alkyl, aryl, hydroxyalkyl, carboxyalkyl, acyl, alkoxycarbonyl, alkylsulfonyl and alkylsulfonate; or $R^9$ is an electron pair;

$R^{10}$ is an alkylene group of $C_1$–$C_6$ carbon atoms, preferably methylene; or $R^8$ and $R^{10}$ together form a heterocyclic ring; or $R^9$ and $R^{10}$ together form a heterocyclic ring, or either $R^9$ or $R^{10}$ forms a heterocyclic ring with $R^4$ or $R^8$; and A is a heteroatom selected from the group consisting of N, O, and S; preferably nitrogen.

These carboxylic acids are disclosed in West, U.S. Pat. No. 5,942,372, especially column 10, line 27, to column 12, line 67, the disclosure of which is incorporated herein by reference. Examples are N-phenyliminodiacetic acid (also called anilino diacetic acid); p-chlorophenyl-iminodiacetic acid; p-bromophenyl-iminodiacetic acid; (p-acetamidophenylimino)diacetic acid; 3-(bis(carboxymethyl)amino)benzoic acid; 4-(bis(carboxymethyl)amino)benzoic acid; 2-((carboxymethyl)phenylamino)benzoic acid; 2-((carboxymethyl)-methylamino)benzoic acid; 2-((carboxymethyl)methylamino)-5-methoxybenzoic acid; 3-(bis(carboxymethylamino)-2-naphthalenecarboxylic acid; N-(4-aminophenyl)-N-(carboxymethyl)glycine; N,N'-1,3-phenylenebisglycine; N,N'-1,3-phenylenebis>-N-(carboxymethyl)glycine; N,N'-1,2-phenylene-bis-N-(carboxymethyl)glycine; N-(carboxymethyl)-N-(4-methoxyphenyl)glycine; N-(carboxymethyl)-N-(3-methoxyphenyl)glycine; N-(carboxymethyl)-N-(3-hydroxyphenyl)glycine; N-(carboxymethyl)-N-(3-chlorophenyl)glycine; N-(carboxymethyl)-N-(4-bromophenyl)glycine; N-(carboxymethyl)-N-(4-chlorophenyl)glycine; N-(carboxymethyl)-N-(4-bromophenyl)glycine; N-(carboxymethyl)-N-(2-chlorophenyl)glycine; N-(carboxymethyl)-N-(4-ethylphenyl)glycine; N-(carboxymethyl)-N-(2,3-dimethylphenyl)glycine; N-(carboxymethyl)-N-(3,4-dimethylphenyl)glycine; N-(carboxymethyl)-N-(3,5-dimethylphenyl)glycine; N-(carboxymethyl)-N-(2,4-dimethylphenyl)glycine; N-(carboxymethyl)-N-(2,6-dimethylphenyl)glycine; N-(carboxymethyl)-N-(4-formylphenyl)glycine; N-(carboxymethyl)-N-ethylanthranilic acid; N-(carboxymethyl)-N-propylanthranilic acid; 5-chloro-N-(carboxymethyl)anthranilic acid; 5-bromo-N-(carboxymethyl)anthranilic acid; N-(2-carboxyphenyl)glycine; o-dianisidine-N,N,N',N'-tetraacetic acid; N,N'-(1,2-ethanediylbis(oxy-2,1-phenylene)bis-N-(carboxymethyl)glycine); 5-amino-2-(carboxymethylthio)benzoic acid; 3-((carboxymethyl)thio)-2-naphthalenecarboxylic acid; and indoleacetic acid, 4-carboxyindoleacetic acid, 5-carboxyindoleacetic acid, 6-carboxyindoleacetic acid, 6-carboxyindoleacetic acid, 7-carboxymethylindoleacetic acid, 6-bromoindoleacetic acid, 6-cyanoindoleacetic acid, and other substituted indoleacetic acids. The most preferred aromatic carboxylic acids are N-phenyliminodiacetic acid; N-(carboxymethyl)-N-phenylglycine; and (3,4-dimethoxyphenylthio)acetic acid. The free radical polymerizable composition typically comprises about 1 to about 10 wt %, more preferably about 1.5 to about 3 wt %, of the carboxylic acid, based on the total weight of the polymerizable composition.

Photothermal Conversion Material

The composition may comprise a photothermal conversion material. Photothermal conversion materials absorb radiation and convert it to heat. Photothermal conversion materials may absorb ultraviolet, visible, and/or infrared radiation and convert it to heat. When infrared radiation is to be used to initiate polymerization, the composition typically comprises a photothermal conversion material.

The photothermal conversion material may be either a dye or pigment, such as a dye or pigment of the squarylium, merocyanine, indolizine, pyrilium, cyanine, or metal diothiolene class. Examples of absorbing pigments are Projet 900, Projet 860 and Projet 830 (all available from the Zeneca Corporation), and carbon black. Dyes, especially dyes with a high extinction coefficient in the range of 750 nm to 1200 nm, are preferred. Absorbing dyes are disclosed in numerous publications, for example, Nagasaka, EP 0,823,327; Van Damme, EP 0,908,397; DeBoer, U.S. Pat. No. 4,973,572; Jandrue, U.S. Pat. No. 5,244,771; and Chapman, U.S. Pat. No. 5,401,618. Examples of useful dyes include: 2-(2-(2-phenylsulfonyl-3-(2-(1,3-dihydro-1,3,3-trimethyl-2H-indol-2ylidene)-ethylidene)-1-cyclohexen-1-yl)-ethenyl)-1,3,3-trimethyl-3H-indolium chloride; 2-(2-(2-thiophenyl-3-(2-(1,3-dihydro-1,3,3-trimethyl-2H-indol-2-ylidene)-ethylidene)-1-cyclohexen-1-yl)-ethenyl)-1,3,3-trimethyl-3H-indolium chloride; 2-(2-(2-thiophenyl-3-(2-(1,3-dihydro-1,3,3-trimethyl-2H-indol-2-ylidene)-ethylidene)-1-cyclopenten-1-yl)-ethenyl)-1,3,3-trimethyl-3H-indolium tosylate; 2-(2-(2-chloro-3-(2-ethyl-(3H-benzthiazole-2-ylidene)-ethylidene)-1-cyclohexen-1yl)-ethenyl)-3-ethyl-benzthiazolium tosylate; 2-(2-(2-phenylthio-3-((1,3-dihydro-1,3,3trimethyl-2H-indol-2-ylidene)ethylidene)-1-cyclohexen-1-yl)ethenyl)-1,3,3-trimethyl-3H indolium chloride; and 2-(2-(2-chloro-3-(2-(1,3-dihydro-1,3,3-trimethyl-2H-indol-2-ylidene)-ethylidene)-1-cyclohexen-1-yl)-ethenyl)-1,3,3-trimethyl-3H-indolium tosylate. Other examples of useful absorbing dyes include: ADS-830A and ADS-1064 (American Dye Source, Montreal, Canada), EC2117 (FEW, Wolfen, Germany), Cyasorb IR 99 and Cyasorb IR 165 (Glendale Protective Technology), Epolite IV-62B and Epolite III-178 (Epoline), PINA-780 (Allied Signal), SpectralR 830A and SpectralR 840A (Spectra Colors), and IR Dye A and IR Dye B, whose structures are shown below.

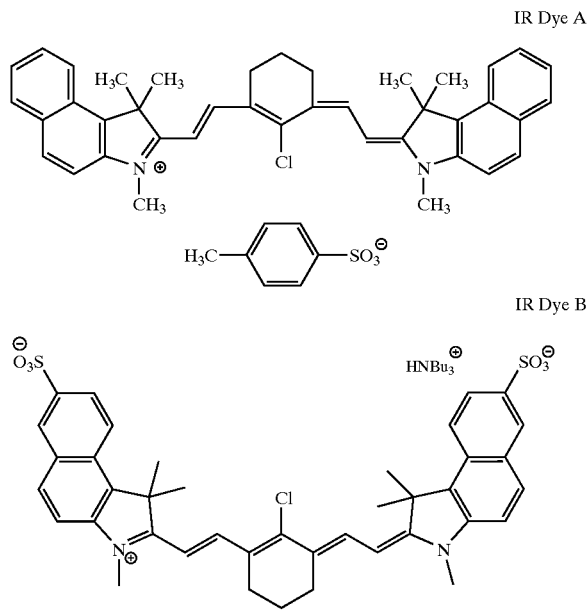

IR Dye A

IR Dye B

The amount of photothermal conversion material in the element is generally sufficient to provide an optical density of at least 0.05, and preferably, an optical density of from about 0.5 to about 2 at the imaging wavelength. The amount of an absorber required to produce a particular optical density can be determined from the thickness of the layer and the extinction coefficient of the absorber at the wavelength used for imaging using Beers law. Depending on the wavelength used for imaging and the absorption of the photothermal conversion material at that wavelength, the composition typically comprises about 0.05 to about 8 wt %, more typically about 0.1 to about 3 wt % of the photothermal conversion material.

Additional Free Polymerizable Monomers

Other free radical polymerizable monomers that are conventional monomers in free radical polymerizable compositions may be added to the QHB-modified free radical polymerizable compound. Typical radical polymerizable monomers are unsaturated esters of alcohols, preferably acrylate and methacrylate esters of polyols. Examples include trimethylol propane tri- and tetraacrylate and methacrylate; the tri- and tetraacrylate and methacrylate esters of ethoxylated trimethylolpropane; diethylene glycol diacrylate and dimethacrylate; triethylene glycol diacrylate and dimethacrylate; 1,4-butanediol diacrylate and dimethacrylate; 2,2,4-trimethyl-1,3-pentanediol diacrylate and dimethacrylate; 1,8-octanediol diacrylate and dimethacrylate; 1,10-decanediol diacrylate and dimethacrylate; polyethylene glycol diacrylate and dimethacrylate; glycerol triacrylate and trimethacrylate; ethylene glycol dimethacrylate; pentaerythritol tri- and tetra-acrylate and methacrylate; dipentaerythriol penta- and hexa-acrylate and methacrylate; tripropylene glycol diacrylate and dimethacrylate; the di-(2-acryloxyethyl)ether and the di-(2-methacryloxyethyl)ether of bisphenol A; ethoxylated bisphenol A diacrylate and dimethacrylate; 1,6-hexanediol diacrylate and dimethacrylate; and neo-pentyl glycol diacrylate and dimethacrylate. Monofunctional monomers, which are sometimes used in combination with multifunctional monomers include, for example, t-butyl acrylate and methacrylate, N,N-diethylaminoethyl acrylate, 2-hydroxyethyl methacrylate, 2-hydroxypropyl methacrylate, 2-ethoxyethyl acrylate and methacrylate, 2-(2-ethoxyethoxy)ethyl acrylate and methacrylate, 2-ethylhexyl acrylate and methacrylate, octyl acrylate and methacrylate, lauryl acrylate and methacrylate, 2-phenoxyethyl acrylate and methacrylate, benzyl acrylate and methacrylate, iso-bornyl acrylate and methacrylate, phenyl acrylate and methacrylate, 2-phenylethyl acrylate and methacrylate, and tetrahydrofurfuryl acrylate and methacrylate. Monomers that may be added to improve the adhesion of a composition containing the monomers include phosphoric acid methacrylate esters such as Kayamer PM-2 (Nippon Kayaku, Tokyo, Japan).

When a monomer or mixture of monomers that do not comprise a QHB group is present, it typically comprises about 30 to 40% of the free radical polymerizable compounds present in the free radical polymerizable composition.

Other Ingredients

The photosensitive composition may comprise other additives depending on the final properties desired. Such additives include plasticizers, rheology modifiers, thermal polymerization inhibitors, tackifiers, colorants, surfactants, antioxidants, and fillers. Surfactants may be added to the composition as coating aids.

A plasticizer may be present to modify adhesion, flexibility, hardness, and other mechanical properties of either the polymerizable composition or the resulting product. The plasticizer should be compatible with other components of the composition. Suitable plasticizers include dibutyl phthalate, dioctyl phthalate, didodecyl phthalate, dioctyl adipate, dibutylsebacate, triacetyl glycerine, and tricresyl phosphate. When present, the plasticizer typically comprises 0.25 to 10 wt % of the composition.

Polymerizable compositions may comprise a small amount of a polymerization inhibitor to inhibit polymerization of the free radical polymerizable compound or compounds during preparation and storage of the composition. Suitable polymerization inhibitors include, for example, hydroquinone, p-methoxyphenol, di-t-butyl-p-cresol, pyrogallol, t-butyl catechol, benzoquinone, 4,4'-thio-bis-(3-methyl-6-t-butylphenol), 2,2'-methylene-bis-(4-methyl-6-t-butylphenol) and N-nitrosophenylhydroxylamine salts. When present, thermal polymerization inhibitor preferably comprises about 0.01 wt % to about 5 wt % of the composition.

The composition may also comprise one or more coloring agents for identification or aesthetic purposes, provided they are compatible with the other ingredients and do not interfere with polymerization. Examples of the coloring agents include pigments such as phthalocyanine-based pigment, azo-based pigment, ethyl violet, crystal violet, azo-based dyes, anthraquinone-based dyes and cyanine-based dyes. When present, the coloring agent typically comprises about 0.5 to about 10 wt % of the composition.

Imageable Elements

In lithographic printing, ink receptive regions, known as image areas, are generated on a hydrophilic surface. When the surface is moistened with water and ink is applied, the hydrophilic regions retain the water and repel the ink, and the ink receptive regions accept the ink and repel the water. The ink is transferred to the surface of a material upon which the image is to be reproduced. Typically, the ink is first transferred to an intermediate blanket, which in turn transfers the ink to the surface of the material upon which the image is to be reproduced.

Imageable elements useful as lithographic printing plates, also called printing plate precursors, comprise a layer of the free radical polymerizable composition (called the imageable layer) over the surface of a hydrophilic substrate. Other layers, such as an underlayer and/or an overcoat layer, may also be present.

Substrate

The substrate will depend on the intended use of the imageable element. Examples of substrates include metals such as aluminum, zinc, titanium, steel, copper, and alloys thereof; alumina-blasted aluminum, anodized aluminum, alumina-blasted polyethylene terephthalate film, polyethylene terephthalate film, e.g., resin-subbed polyethylene terephthalate film, polyvinyl alcohol-coated paper, crosslinked polyester-coated paper, nylon, glass, cellulose acetate film, and heavy paper such as lithographic paper.

For the preparation lithographic printing plates, the substrate has at least one hydrophilic surface. It comprises a support, which may be any material conventionally used to prepare imageable elements useful as lithographic printing plates. The support is preferably strong, stable and flexible. It should resist dimensional change under conditions of use so that color records will register in a full-color image. Typically, it can be any self-supporting material, including, for example, polymeric films such as polyethylene terephthalate film, ceramics, metals, or stiff papers, or a lamination of any of these materials. Metal supports include aluminum, zinc, titanium, steel, copper, and alloys thereof.

Typically, polymeric films contain a sub-coating on one or both surfaces to modify the surface characteristics to enhance the hydrophilicity of the surface, to improve adhesion to subsequent layers, to improve planarity of paper substrates, and the like. The nature of this layer or layers depends upon the substrate and the composition of subsequent coated layers. Examples of subbing layer materials are adhesion-promoting materials, such as alkoxysilanes, aminopropyltriethoxysilane, glycidoxypropyltriethoxysilane and epoxy functional polymers, as well as conventional subbing materials used on polyester bases in photographic films.

The surface of an aluminum support may be treated by techniques known in the art, including physical graining, electrochemical graining, chemical graining, and anodizing. The substrate should be of sufficient thickness to sustain the wear from printing and be thin enough to wrap around a printing form, typically from about 100 to about 600 μm. Typically, the substrate comprises an interlayer between the aluminum support and the imageable layer. The interlayer may be formed by treatment of the support with, for example, silicate, dextrine, hexafluorosilicic acid, phosphate/fluoride, polyvinyl phosphonic acid (PVPA) or polyvinyl phosphonic acid copolymers.

The back side of the substrate (i.e., the side opposite the underlayer and imageable layer) may be coated with an antistatic agent and/or a slipping layer or matte layer to improve handling and "feel" of the imageable element.

As will be apparent to those skilled in the art, for other applications, other supports may be used. For the preparation of printed circuit boards, for example, a flexible support such as a polyethylene terephthalate film may be used. The element is laminated to a printed circuit board precursor, typically a plate that is a copper coating on fiberboard, prior to imaging.

Underlayer

The imageable element may comprise an underlayer between the hydrophilic surface of the substrate and the imageable layer. After imaging, it is removed by the developer to expose the underlying hydrophilic surface of the substrate. It is preferably soluble in the developer to prevent sludging of the developer.

The underlayer comprises a first polymeric material. The first polymeric material is preferably soluble in an alkaline developer. In addition, the first polymeric material is preferably insoluble in the solvent used to coat the imageable layer so that the imageable layer can be coated over the underlayer without dissolving the underlayer. Polymeric materials useful as the first polymeric material include those that contain an acid and/or phenolic functionality, and mixtures of such materials. Useful polymeric materials include carboxy functional acrylics, vinyl acetate/crotonate/vinyl neodecanoate copolymers, styrene maleic anhydride copolymers, phenolic resins, maleated wood rosin, and combinations thereof. Underlayers that provide resistance both to fountain solution and aggressive washes are disclosed in Shimazu, U.S. Pat. No. 6,294,311, incorporated herein by reference.

Particularly useful polymeric materials are copolymers that comprise N-substituted maleimides, especially N-phenylmaleimide; polyvinylacetals; methacrylamides, especially methacrylamide; and acrylic and/or methacrylic acid, especially methacrylic acid. More preferably, two functional groups are present in the polymeric material, and most preferably, all three functional groups are present in the polymeric material. The preferred polymeric materials of this type are copolymers of N-phenylmaleimide, methacrylamide, and methacrylic acid, more preferably those that contain about 25 to about 75 mol %, preferably about 35 to about 60 mol % of N-phenylmaleimide; about 10 to about 50 mol %, preferably about 15 to about 40 mol % of methacrylamide; and about 5 to about 30 mol %, preferably about 10 to about 30 mol %, of methacrylic acid. Other hydrophilic monomers, such as hydroxyethyl methacrylate, may be used in place of some or all of the methacrylamide. Other alkaline soluble monomers, such as acrylic acid, may be used in place of some or all of the methacrylic acid.

These polymeric materials are soluble in alkaline developers. In addition, they are soluble in a methyl lactate/methanol/dioxolane (15:42.5:42.5 wt %) mixture, which can be used as the coating solvent for the underlayer. However, they are poorly soluble in solvents such as acetone, which can be used as solvents to coat the imageable layer on top of the underlayer without dissolving the underlayer. These polymeric materials are typically resistant to washes with 80 wt % diacetone alcohol/20 wt % water.

Another group of preferred polymeric materials for the first polymeric material are alkaline developer soluble copolymers that comprise a monomer that has a urea bond in its side chain (i.e., a pendent urea group), such as are disclosed in Ishizuka, U.S. Pat. No. 5,731,127. These copolymers comprise about 10 to 80 wt %, preferably about 20 to 80 wt %, of one of more monomers represented by the general formula:

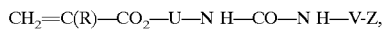

$CH_2=C(R)-CO_2-U-N\ H-CO-N\ H-V-Z$, in which R is —H or —CH$_3$; U is a bivalent linking group; V is a substituted or unsubstituted bivalent aromatic group; and Z is —OH, —COOH, or —SO$_2$NH$_2$.

R is preferably —CH$_3$. Preferably U is a substituted or unsubstituted alkylene group, substituted or unsubstituted phenylene (C$_6$H$_4$) group, or substituted or unsubstituted naphthalene (C$_{10}$H$_6$) group; such as —(CH$_2$)$_n$—, in which n is 2 to 8; 1,2-, 1,3-, and 1,4-phenylene; and 1,4-, 2,7-, and 1,8-naphthalene. More preferably U is unsubstituted and even more preferably n is 2 or 3; most preferably U is —(CH$_2$CH$_2$)—. Preferably V is a substituted or unsubstituted phenylene group or substituted or unsubstituted naphthalene group; such as 1,2-, 1,3-, and 1,4-phenylene; and 1,4-, 2,7-, and 1,8-naphthalene. More preferably V is unsubstituted, most preferably unsubstituted 1,4-phenylene. Z is —OH, —COOH, or —SO$_2$NH$_2$, preferably —OH. A preferred monomer is:

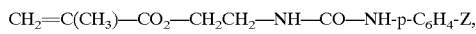

$CH_2=C(CH_3)-CO_2-CH_2CH_2-NH-CO-NH-p-C_6H_4-Z$, in which Z is —OH, —COOH, or —SO$_2$NH$_2$, preferably —OH.

In the synthesis of a copolymer, one or more of the urea group containing monomers may be used. The copolymers also comprise 20 to 90 wt % other polymerizable monomers, such as maleimide, acrylic acid, methacrylic acid, acrylic esters, methacrylic esters, acrylonitrile, methacrylonitrile, acrylamides, and methacrylamides. A copolymer that comprises in excess of 60 mol % and not more than 90 mol % of acrylonitrile and/or methacrylonitrile in addition to acrylamide and/or methacrylamide provides superior physical properties. More preferably the alkaline soluble copolymers comprise 30 to 70 wt % urea group containing monomer; 20 to 60 wt % acrylonitrile or methacrylonitrile, preferably acrylonitrile; and 5 to 25 wt % acrylamide or methacrylamide, preferably methacrylamide. These polymeric materials are typically resistant to washes with 80 wt % 2-butoxyethanol/20 wt % water.

The polymeric materials described above are soluble in alkaline developers. In addition, they are soluble in polar solvents, such as ethylene glycol monomethyl ether, which can be used as the coating solvent for the underlayer. However, they are poorly soluble in less polar solvents, such as 2-butanone (methyl ethyl ketone), which can be used as a solvent to coat the imageable layer over the underlayer without dissolving the underlayer.

Both these groups of polymeric materials can be prepared by methods, such as free radical polymerization, well known to those skilled in the art. Synthesis of copolymers that have urea bonds in their side chains is disclosed, for example, in Ishizuka, U.S. Pat. No. 5,731,127.

Another group of polymeric materials that are useful in the underlayer include alkaline developer soluble copolymers that comprise about 10 to 90 mol % of a sulfonamide monomer unit, especially those that comprise N-(p-aminosulfonylphenyl)methacrylamide, N-(m-aminosulfonylphenyl)methacrylamide N-(o-aminosulfonylphenyl)methacrylamide, and/or the corresponding acrylamide. Useful alkaline developer soluble polymeric materials that comprise a pendent sulfonamide group, their method of preparation, and monomers useful for their preparation, are disclosed in Aoshima, U.S. Pat. No. 5,141,838. Particularly useful polymeric materials comprise (1) the sulfonamide monomer unit, especially N-(p-aminosulfonylphenyl)methacrylamide; (2) acrylonitrile and/or methacrylonitrile; and (3) methyl methacrylate and/or methyl acrylate. These polymeric materials are typically resistant to washes with 80 wt % 2-butoxyethanol/20 wt % water.

When the imageable element comprises an underlayer, the photothermal conversion material may be present in the underlayer. Alternatively, the photothermal conversion material may be located in a separate absorber layer between the underlayer and the imageable layer.

Overcoat Layer

An essentially oxygen-impermeable overcoat layer, which is soluble in the developer and transparent to to the radiation used for imaging, may be applied over the imageable layer. This layer is not only useful as an oxygen barrier but also protects the imageable element against ablation during imaging. The overcoat layer also improves the scratch resistance of the imageable element, which makes it easier to handle.

Overcoat layers are described in WO 99/06890. Preferred binders for the overcoat layer are water-soluble polymers such as polyvinyl alcohol, polyvinyl alcohol/polyvinyl acetate copolymers, polyvinyl pyrrolidone, vinyl pyrrolidone/vinyl acetate copolymers, polyvinyl methyl ether, ring-opened copolymers of maleic anhydride and co-monomers such as methyl vinyl ether, polyacrylic acid, gelatine, cellulose ethers, and mixtures thereof. Most preferred is polyvinyl alcohol. The coating weight of the overcoat layer is preferably 0.1 to 6 g/m$^2$, and more preferably 0.5 to 4 g/m$^2$.

The overcoat layer may also contain coloring agents (water soluble dyes) that do not absorb in the imaging wavelength region, typically between 800 and 1200 nm, but efficiently absorb visible light, thereby improving the stability of the element to ambient visible radiation. To improve the adhesion of the overcoat layer to the imageable layer, an adhesion promoter can be added to the overcoat layer formulation. One example for such an adhesion promoter is poly(vinyl imidazole) as disclosed in WO 99/06890.

Coversheet

The imageable element may also comprise a temporary coversheet over the imageable layer. The coversheet protects the imageable layer during storage and handling. Examples of suitable materials for the coversheet include thin films of polystyrene, polyethylene, polypropylene, polycarbonate, fluoropolymers, polyamide or polyester, which can be subbed with release layers.

Preparation of the Imageable Elements

The imageable element may be prepared by sequentially applying the underlayer, if present, over the hydrophilic surface of the substrate; applying the imageable layer over the underlayer, or over the substrate if the underlayer is not present, and applying the overcoat layer, if present, over the imageable layer using conventional techniques.

The terms "solvent" and "coating solvent" include mixtures of solvents. They are used although some or all of the materials may be suspended or dispersed in the solvent rather than in solution. Selection of the solvents will depend on the ingredients present in these layers. If present, the underlayer may be applied over the hydrophilic surface by any conventional method, such as coating or lamination. Typically the ingredients are dispersed or dissolved in a suitable coating solvent, and the resulting mixture coated by conventional methods, such as spin coating, bar coating, gravure coating, die coating, or roller coating.

If more than one layer is to be applied, to prevent these layers from dissolving and mixing during coating, the overlying layer is preferably coated from a solvent in which the underlying layer is essentially insoluble. Thus, when the imageable layer is coated over an underlayer, the coating solvent for the imageable layer should be a solvent in which the ingredients in the imageable layer are sufficiently soluble that the imageable layer can be formed and in which the materials in the underlayer are essentially insoluble. An intermediate drying step, i.e., drying the underlayer, if present, to remove coating solvent before coating the imageable layer over it, may also be used to prevent mixing of the layers. The coversheet, if present, is typically laminated over the imageable layer or, if present, the barrier layer.

Imaging and Development of the Imageable Elements

The coversheet, if present, is removed before imaging, typically by being peeled off. For some applications, such as photoresists for printed circuit boards, the resulting element may be laminated to a receptor, such as a printed circuit precursor, prior to imaging.

The imageable element may be imaged with actinic radiation to which the free radical generating system is sensitive. Any convenient source or sources of actinic radiation providing wavelengths in the region of the spectrum to which the free radical generating system is sensitive may be used to activate free radical polymerization. Conventional ultraviolet/visible light sources include fluorescent lamps, mercury lamps, metal additive lamps, and arc lamps. Imaging with these light sources is typically carried out by exposure through a photomask.

Direct digital imaging, which obviates the need for exposure through a photomask, is becoming increasingly important in the printing industry. For ultraviolet and/or visible imaging, sources that include ultraviolet and/or visible lasers, such as xenon, argon ion, and ionized neon lasers, as well as tunable dye lasers and the frequency doubled neodymium: YAG laser.

Thermal direct digital imaging may be carried out by well-known methods. The element may be thermally imaged with a laser or an array of lasers emitting modulated near infrared or infrared radiation in a wavelength region that is absorbed by the imageable element. Infrared radiation, especially infrared radiation in the range of about 800 nm to about 1200 nm, typically at 830 nm or 1064 nm, is typically used for imaging thermally imageable elements. Imaging is conveniently carried out with a laser emitting at about 830 nm or at about 1064 nm. Suitable commercially available imaging devices include image setters such as the Creo Trendsetter (CREO) and the Gerber Crescent 42T (Gerber).

Alternatively, the element may be thermally imaged using a conventional apparatus containing a thermal printing head. An imaging apparatus suitable for use in conjunction with these elements includes at least one thermal head but would usually include a thermal head array, such as a TDK Model No. LV5416 used in thermal fax machines and sublimation printers or the GS618-400 thermal plotter (Oyo Instruments, Houston, Tex., USA). Elements that are to be imaged with a thermal printing head do not require a photothermal conversion material in the element. However, elements that comprise a thermal printing head may be imaged with a thermal printing head.

Imaging produces an imaged element, which comprises a latent image of imaged (exposed) regions and unimaged (unexposed) regions. Development of the imaged element in a suitable developer to form a lithographic printing plate, or printing form, converts the latent image to an image by removing the unimaged (uexposed) regions, revealing the hydrophilic surface of the underlying substrate.

The developer may be any liquid or solution that can penetrate and remove the unexposed regions of the imageable layer, and, if present, the underlying regions the underlayer, without substantially affecting the complimentary exposed regions. Suitable developers depend on the solubility characteristics of the ingredients present in the imageable element. It is possible to tailor the solubility characteristics of the photopolymerizable composition so that typical developers for negative working photosensitive plates can be used. Such negative developers typically consist of water, surfactants, organic solvents and neutralizers. Examples of suitable surfactants are sodium octyl sulfonate and PELEX® NBL (an aqueous solution of sodium n-butyl naphthalene sulfonate, available from the High Point Chemical Corporation). Example of solvents are benzyl alcohol, 2-phenoxyethanol, and 2-phenoxypropanol. Examples of neutralizers are sodium carbonate, triethanol amine, diethanolmethylamine, sodium phosphate and sodium hydroxide.

Development is carried out for a long enough time to remove the unimaged regions of the imageable layer, and, if present, the underlying regions of the underlayer, but not long enough to remove the imaged regions of the imageable layer. The developer is typically applied to the imaged imageable element by spraying the element with sufficient force to remove the unexposed regions. Alternatively, development may be carried out in a processor or the imaged imageable element may be brushed with the developer. In each instance, a printing plate is produced. Development may conveniently be carried out in a commercially available spray-on processor, such as an 85 NS (Kodak Polychrome Graphics).

INDUSTRIAL APPLICABILITY

The QHB-modified compounds may used to form free radical polymerizable compositions. The free radical polymerizable compositions may be used in any of the well-known applications of free radical polymerizable compositions. Thermally curable compositions can be used in heat-curable coatings, thermally curable adhesives, and thermally curable molding materials. If the free radical polymerizable composition is used as a radiation curable coating, it may be polymerized ("cured" or "hardened") by overall exposure with ultraviolet, visible, and/or infrared radiation matched to the sensitivity of the free radical generating system using methods well known to those skilled in the art of radiation curable coatings.

Imaging applications of imageable free radical polymerizable compositions are discussed in, for example, in "Photopolymers: Radiation Curable Imaging Systems," by B. M. Monroe, in *Radiation Curing: Science and Technology*, S. P. Pappas, Ed., Plenum, New York, 1992, pp. 399–440, and "Polymer Imaging" by A. B. Cohen and P. Walker, in *Imaging Processes and Material*, J. M. Sturge, et al., Eds., Van Nostrand Reinhold, New York, 1989, pp. 226–262. These include, for example, lithographic, letterpress, and flexographic printing plate precursors; photoresists and solder masks for printed circuit boards and for semiconductor and other device fabrication; and off-press color proofing systems.

Printing plates that comprise the free radical polymerizable compositions of this invention have the following advantages: high imaging speed, excellent chemical resistance after imaging, high resolution due to the absence of a conventional binder, and good ink receptivity due to the absence of the hydrophilic groups on polymeric binders that are necessary for developability. Once the imageable element has been imaged and processed to form a printing plate, printing can be carried out by applying a fountain solution and then a lithographic ink to the image on its surface. Fountain solution is taken up by the non-imaged regions, i.e., the surface of the substrate exposed by imaging and development, and the ink is taken up by the exposed regions (image regions). The ink is transferred to a suitable receiving material (such as cloth, paper, metal, glass or plastic) either directly or indirectly using an offset printing blanket to provide a desired impression of the image thereon. The imaging members can be cleaned between impressions, if desired, using conventional cleaning means.

The advantageous properties of this invention can be observed by reference to the following examples, which illustrate but do not limit the invention.

EXAMPLES

In the Examples, "coating solution" refers to the mixture of solvent or solvents and additives coated, even though some of the additives may be in suspension rather than in solution, and "total solids" refers to the total amount of nonvolatile material in the coating solution even though some of the additives may be nonvolatile liquids at ambient temperature. Except where indicated, the indicated percentages are percentages by weight based on the total solids in the coating solution. "Molecular weight" refers to weight average molecular weight measured by size exclusion chromatography.

Glossary

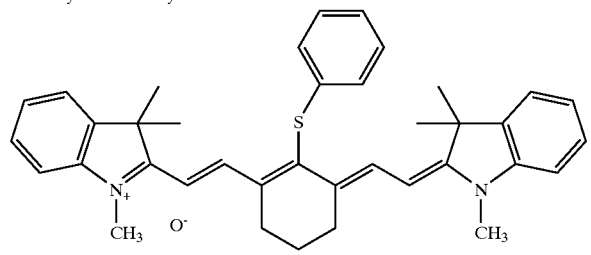

| | |
|---|---|
| DESMODUR® N-100 | Solvent-free, aliphatic polyisocyanate resin, trimer of hexamethylene diisocyanate; NCO content, 21.0 ± 0.2% (Bayer Coatings and Colorants, Pittsburgh, PA, U.S.A) |
| DMAC | Dimethylacetamide |
| METHYL CELLOSOLVE® | 2-methoxyethanol (Dow, Midland, MI, U.S.A) |
| IR-Dye 66e | 2-{2-(2-Phenylthio-3-((1,3-dihydro-1,3,3 trimethyl-2H-indol-2-ylidene)ethylidene)-1-cyclohexen-1-yl) ethenyl}-1,3,3-trimethyl-3H indolium chloride; $\square_{max}$ = 788 nm (Kodak Polychrome Graphics, Freundorfer, Munich, Germany) |
| PETA | Pentaerythritol triacrylate |

Dye 66e

Example 1

This example illustrates preparation of a QHB-modified free radical polymerizable compound from DESMODUR® N-100; 2-amino-4-hydroxy-6-methyl pyrimidine (methyl isocytocine); PETA; and 1,4-butanediol in the equivalent ratio 9/2.5/4/2.68 (R-value=OH/NCO=1.02) in DMAC at 40% non-volatiles.

DMAC (152.4 g), DESMODUR® N-100 (85.95 g; 0.45 eq) and 2-amino-4-hydroxy-6-methyl pyrimidine (15.64 g; 0.125 eq) (Aldrich, Milwaukee, Wis., USA) were charged in a four-necked 1-L flask fitted with a heating mantle, temperature controller, mechanical stirrer, condenser, nitrogen inlet and pressure equalized funnel. The reaction mixture was allowed to heat slowly to about 87° C. to 90° C. The % NCO was 13.2 versus 13.44 (theoretical). The viscosity, measured using a Gardner Bubble Viscometer, was <50 cps.

The reaction mixture was cooled to 40° C. and premixture of DMAC (135.6 g), PETA (89.05 g; 0.2 eq), hydroquinone (0.38 g), dibutyltin dilaurate (0.3 g) were added over 30 min. The temperature was slowly raised to 60° C. while additional dibutyltin dilaurate (0.3 g) was added. Five hours later, the % NCO was 2.8 versus 2.74 (theoretical) and viscosity was <50 cps.

The reaction mixture was cooled to 50° C. and premixture of DMAC (9.0 g), 1,4-butane diol (6.03 g; 0.1338 eq), and dibutyltin dilaurate (0.3 g) were added over 30 min. Five hours later, the % NCO was 0.0 based on titration and FT-IR (2275 cm$^{-1}$). The viscosity, measured using a Gardner Bubble Viscometer, was 130 cps. The % non-volatiles were 40%. The reaction mixture is clear liquid at room temperature. The next day, the room temperature viscosity, measured using a Gardner Bubble Viscometer, was 270 cps and remained the same at room temperature for longer time.

Example 2

This example illustrates preparation of a QHB-modified free radical polymerizable compound from DESMODUR® N-100; 2-amino-4-hydroxy-6-methyl pyrimidine; PETA; and 1,4-butanediol in the equivalent ratio 9/2.95/4/2.5 (R-value =OH/NCO=1.05) in DMAC at 35% non-volatiles. The compound was end capped with 2-methoxyethanol.

DMAC (137.7 g), DESMODUR® N-100 (85.95 g; 0.45 eq), and dibutyl tin dilaurate (0.1 g) were charged in a four-necked 1-L flask fitted with a heating mantle, temperature controller, mechanical stirrer, condenser, nitrogen inlet and pressure equalized funnel. 1,4-Butanediol (5.63 g; 0.125 eq) was added over 30 min and the reaction mixture heated to 40° C. The % NCO was 14.81 versus 14.86 (theoretical) and viscosity was <50 cps at 40% non-volatiles.

A pre-mixture of DMAC (27.7 g) and 2-amino, 4-hydroxy, 6-methyl pyrimidine (18.45 g; 0.147 eq) was added. The temperature was increased in 10° C. increments every 10 min until the reaction mixture became clear at 87° C. The % NCO was 6.42 versus 6.76 (theoretical) and viscosity was 8100 cps at 40% non-volatiles.

The reaction mixture was cooled to 50° C. and premixture DMAC (134.91 g), PETA (89.05 g; 0.2 eq), hydroquinone (0.39 g), and dibutyl tin dilaurate (0.33 g) were added over 30 min. DMAC (71.4 g) was added to reduce the viscosity. Non-volatiles were reduced to 35%. The temperature was slowly raised to 60° C. and additional dibutyl tin dilaurate (0.3 g) added. Six hours later the % NCO was 0.40 and viscosity was 884 cps.

METHYL CELLOSOLVE® (5 g) was added. The % NCO was 0.0 based on titration and FT-IR (2275 cm$^{-1}$). The viscosity, measured using a Gardner Bubble Viscometer, was 900 cps. The % non-volatiles were 35%. The reaction mixture was a clear liquid at room temperature. The next day, the room temperature viscosity, measured using a Gardner Bubble Viscometer, was 1240 cps and remained the same at room temperature for longer time.

Examples 3 and 4

Coating solutions of the composition shown in Table 1 were coated on a support using a whirl coater. The support was brush-grained and phosphoric acid anodized aluminum that had been subbed by a polyacrylic acid solution. The resulting element was dried at 80° C. for 5 min. The dry coating weight of the resulting imageable layer was 2 g/m$^2$.

TABLE 1

| | Example 3 | Example 4 |
|---|---|---|
| QHB-Modified Compound of Example 1[a] | 27.48 g | — |
| QHB-Modified Compound of Example 2[b] | — | 21.59 g |
| 2-(4-Methoxyphenyl)-4,6-bis(trichloromethyl)-s-triazine | 0.576 g | 0.396 g |
| N-Phenyliminodiacetic acid | 0.312 g | 0.2145 g |
| IR-Dye 66e | 0.12 g | 0.0825 g |
| DMAC | 39.45 g | 26.15 g |
| METHYL CELLOSOLVE® | 65.76 g | 43.86 g |
| Dioxolane | 26.30 g | 17.54 g |

[a]40% Non-volatiles
[b]35% Non-volatiles

The resulting imageable elements, comprising the imageable layer on the support, were imaged with a Creo Trendsetter 3244 image setter (CreoScitex, Burnaby, British Columbia, Canada) using 830 nm infra-red laser at a laser power of 10.75 W and a series of drum speed from 69 to 138 rpm (exposure ranged from 200 to 400 mJ/cm$^2$). With Scorpio negative developer (Kodak Polychrome Graphics), 15 sec dwell and rub time was required for each imaged imageable element. With Fuji DN-5H negative developer, 30 sec dwell and rub time was required. When a test pattern with a resolution 3/97 at 200 line per inch was used, the test pattern was faithfully reproduced at 200 mJ/cm$^2$ exposure and the 10 micron pixel was resolved.

Example 5

The imageable element of Example 3 was imaged with a Creo Trendsetter 3244 image setter at 140 mJ/cm$^2$ using a test pattern having 1–99% dots of a 175 lines per inch screen. After development with Scorpio developer, all dots from 1 to 99% in the test pattern were reproduced.

Example 6

This example illustrates that the imageable element can be imaged by ultraviolet radiation by exposure through a negative.

The imageable element of Example 3 was imaged with a Pako Imaging System exposure unit having a 5 KW B-1406-05 photopolymer lamp (Bergess Industries). The element was contact exposed with at 50 mJ/cm$^2$ of ultraviolet radiation through a negative having a UGRA step wedge and developed with the Scorpio negative developer with 15 sec of dwell and 15 sec of rub time. Results: UGRA Scale—inked (⅕=solid/tail), and Resolution—inked ⅘ to complete open ⅘, i.e. the 4 micron line is retained and a 6 micron gap in a solid area is open after development.

Having described the invention, we now claim the following and their equivalents.

What is claimed is:

1. A QHB-modified free radical polymerizable compound having the structure:

in which:

Q is a moiety that comprises a QHB unit;

P is a moiety that comprises more than one free radical polymerizable group;

B is a supporting backbone;

$m \geq 1$; and $n \geq 1$.

2. The QHB-modified free radical polymerizable compound of claim 1 in which the QHB unit is selected from:

(I) 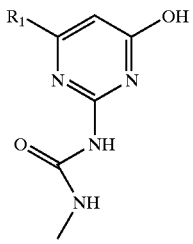

(II) 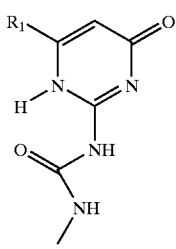

(III) 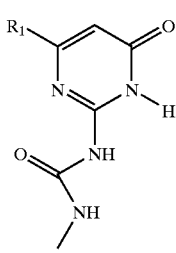

(IV) 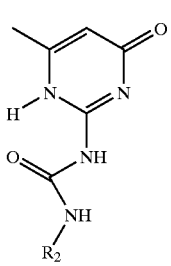

(V) 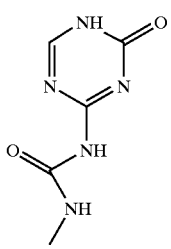

(VI) 

in which $R_1$ is hydrogen or an alkyl group of 1 to 10 carbon atoms and $R_2$ is a residue from an isocyanate compound.

3. The QHB-modified free radical polymerizable compound of claim 2 in which the QHB unit is selected from structures I, II, and III, and $R_1$ is methyl.

4. A free radical polymerizable composition comprising:
a free radical generating system; and
a QHB-modified free radical polymerizable compound having the structure:

$$(P)_m B(Q)_n$$

in which:
Q is a moiety that comprises a QHB unit;
P is a moiety that comprises more than one free radical polymerizable group;
B is a supporting backbone;
$m \geq 1$; and
$n \geq 1$.

5. The free radical polymerizable composition of claim 4 in which the free radical generating system is a thermal initiator.

6. The free radical polymerizable composition of claim 4 in which the free radical polymerizable composition additionally comprises a photothermal conversion material.

7. The free radical polymerizable composition of claim 4 in which the free radical generating system comprises:
a polyhaloalkyl-substituted free radical producing compound; and
a carboxylic acid of the following formula:

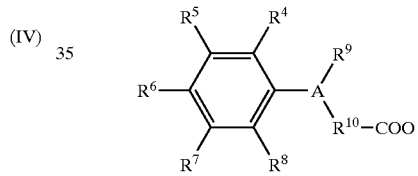

in which:
$R^4$, $R^5$, $R^6$, $R^7$ and $R^8$ are each independently selected from the group consisting of hydrogen, alkyl, aryl, halogen, alkoxy, hydroxyalkyl, carboxy, carboxyalkyl, alkylthio, alkylsulfonyl, sulfonic, aikylsulfonate, dialkylamino, acyl, alkoxycarbonyl, cyano and nitro; or $R^4$ and $R^5$, $R^5$ and $R^6$, $R^6$ and $R^7$, or $R^7$ and $R^8$ together form an aromatic or aliphatic ring;
$R^9$ is selected from the group consisting of hydrogen, alkyl, aryl, hydroxyalkyl, carboxyalkyl, acyl, alkoxycarbonyl, alkylsulfonyl and alkylsulfonate; or $R^9$ is an electron pair;
$R^{10}$ is an alkylene group of $C_1$–$C_6$ carbon atoms, preferably methylene; or $R^8$ and $R^{10}$ together form a heterocyclic ring; or $R^9$ and $R^{10}$ together form a heterocyclic ring, or either $R^9$ or $R^{10}$ forms a heterocyclic ring with $R^4$ or $R^8$; and
A is a heteroatom selected from the group consisting of N, O, and S.

8. The free radical polymerizable composition of claim 7 in which the carboxylic acid is selected from the group consisting of N-phenyliminodiacetic acid; N-(carboxymethyl)-N-phenylglycine; and (3,4-dimethoxyphenylthio)acetic acid.

9. The free radical polymerizable composition of claim 8 in which the QHB unit is selected from:

(I) 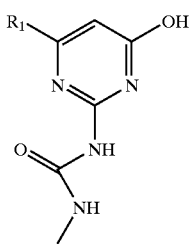

(II) 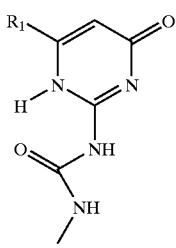

(III) 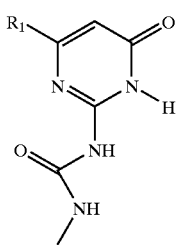

(IV) 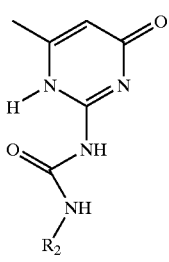

(V) 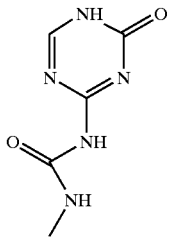

(VI) 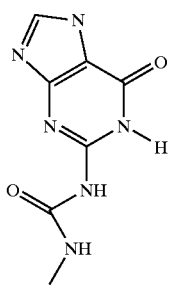

in which $R_1$ is hydrogen or an alkyl group of 1 to 10 carbon atoms and $R_2$ is a residue from an isocyanate compound.

10. The free radical polymerizable composition of claim 9 in which the free radical polymerizable composition additionally comprises a photothermal conversion material.

11. The free radical polymerizable composition of claim 10 in which the QHB unit is selected from structures I, II, and III, and $R_1$ is methyl.

12. The free radical polymerizable composition claim 11 in which n is at least 2, and P comprises 2 to 5 free radical polymerizable groups.

13. The free radical polymerizable composition of claim 12 in which the free radical polymerizable groups each comprise a $C=CH_2$ structural unit.

14. An imageable element comprising:

a substrate; and a layer of a polymerizable composition over the substrate;

in which the polymerizable composition comprises:

a free radical generating system; and a QHB-modified free radical polymerizable compound having the structure:

$$(P)_m B(Q)_n$$

in which:

Q is a moiety that comprises a QHB unit;

P is a moiety that comprises more than one free radical polymerizable group;

B is a supporting backbone;

$m \geq 1$; and $n \geq 1$.

15. The imageable element of claim 14 in which the QHB unit is selected from:

(I) 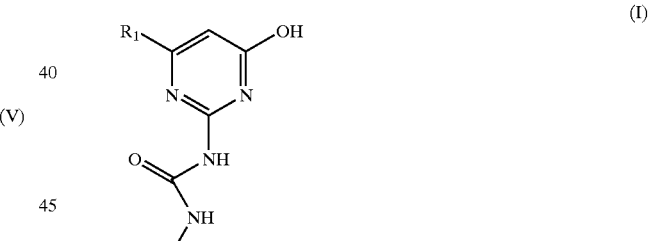

(II) 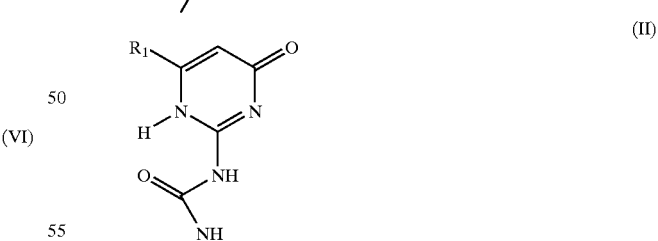

(III) 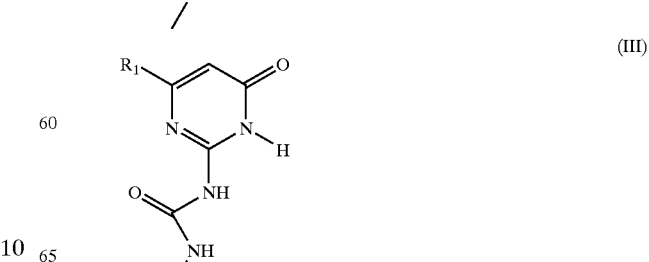

(IV)

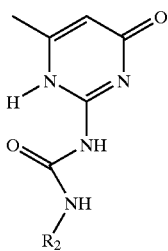

(V)

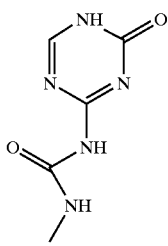

(VI)

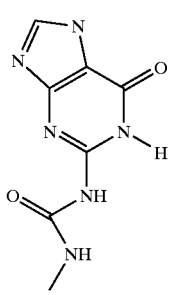

in which $R_1$ is hydrogen or an alkyl group of 1 to 10 carbon atoms and $R_2$ is a residue from an isocyanate compound.

16. The imageable element of claim 15 in which the QHB unit is selected from structures I, II, and III, and $R_1$ is methyl.

17. The imageable element claim 16 in which-n is at least 2, and P comprises 2 to 5 free radical polymerizable groups.

18. The imageable element of claim 17 in which the free radical polymerizable groups each comprise a C=CH$_2$ structural unit.

19. The imageable element claim 18 in which n is 2, and P comprises 2 or 3 free radical polymerizable groups.

20. The imageable element of claim 19 in which the free radical generating system comprises a polyhaloalkyl-substituted free radical producing compound; and a carboxylic acid is selected from the group consisting of N-phenyliminodiacetic acid; N-carboxymethyl)-N-phenylglycine; and (3,4-dimethoxyphenylthio)acetic acid.

21. The imageable element of claim 20 in which the free radical polymerizable composition additionally comprises a photothermal conversion material.

22. The imageable element of claim 14 additionally comprising an underlayer between the substrate and the imageable layer.

23. A method for forming an image, the method comprising:
imaging an imageable element and forming an imaged imageable element comprising imaged regions and complementary unimaged regions; and
developing the imaged imageable element and removing the unexposed regions;
in which:

the imageable element comprises:
a substrate; and
a layer of a polymerizable composition over the substrate; the polymerizable composition comprising:
a free radical generating system; and
a QHB-modified free radical polymerizable compound having the structure:

in which:
Q is a moiety that comprises a QHB unit;
P is a moiety that comprises more than one free radical polymerizable group;
B is a supporting backbone;
m≧1; and
n≧1.

24. The method of claim 23 in which imaging is carried out with heat or infrared radiation.

25. The method of claim 23 in which imaging is carried out with ultraviolet laser or by exposure with ultraviolet radiation through a photomask.

26. The method of claim 23 in which the QHB unit is selected from:

(I)

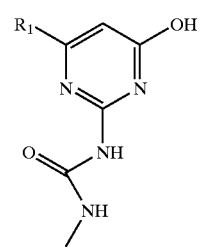

(II)

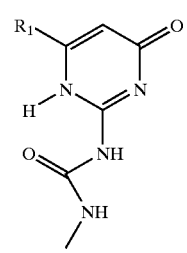

(III)

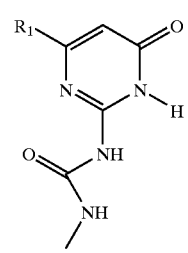

(IV)

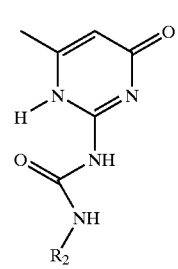

-continued (V)
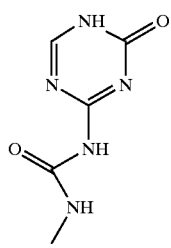

(VI)
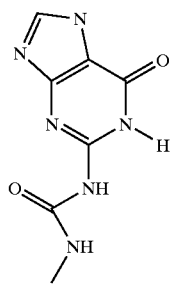

in which $R_1$ is hydrogen or an alkyl group of 1 to 10 carbon atoms and $R_2$ is a residue from an isocyanate compound.

27. The method of claim 26 in which the QHB unit is selected from structures I, II, and III, and $R_1$ is methyl.

28. The method of claim 27 in which n is at least 2, and P comprises 2 to 5 free radical polymerizable groups.

29. The method of claim 28 in which the free radical polymerizable groups each comprise a C=CH2 structural unit.

30. The method of claim 29 in which n is 2, and P comprises 2 or 3 free radical polymerizable groups.

31. The method of claim 30 in which the free radical generating system comprises a polyhaloalkyl-substituted free radical producing compound; and a carboxylic acid is selected from the group consisting of N-phenyliminodiacetic acid; N-(carboxymethyl)-N-phenylglycine; and (3,4-dimethoxyphenylthio)acetic acid.

32. The method of claim 31 in which imaging is carried out with heat or infrared radiation.

33. The method of claim 31 in which imaging is carried out with ultraviolet laser or by exposure with ultraviolet radiation through a photomask.

34. A QHB-modified free radical polymerizable compound having the structure:

$(P)_m B(Q)_n$ in which:

Q is a moiety that comprises a QHB unit:

P is a moiety that comprises 1 to 5 free radical polymerizable groups;

B is a supporting backbone;

$m \geq 1$; and $n \geq 2$.

35. The QHB-modified free radical polymerizable compound of claim 34 in which n is 2, and P comprises 2 or 3 free radical polymerizable groups.

36. The QHB-modified free radical polymerizable compound of claim 35 in which the QHB unit is selected from:

(I)
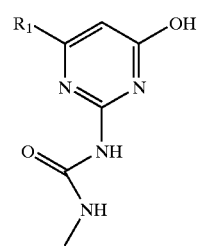

(II)
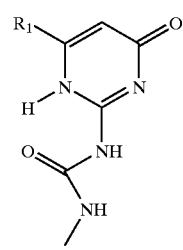

(III)
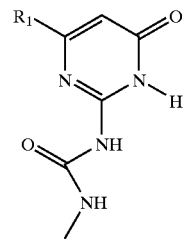

(IV)
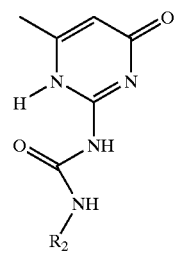

(V)
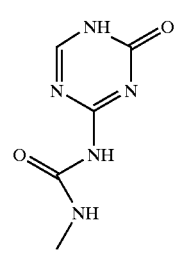

(VI)
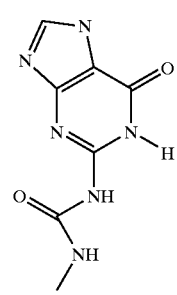

in which $R_1$ is hydrogen or an alkyl group of 1 to 10 carbon atoms and $R_2$ is a residue from an isocyanate compound.

37. The QHB-modified free radical polymerizable compound of claim 36 in which the QHB unit is selected from structures I, II, and III, and $R_1$ is methyl.

38. A QHB-modified free radical polymerizable compound having the structure:

$(P)_m B(Q)_n$ in which:

Q is a moiety that comprises a QHB unit;

P is a moiety that comprises at least one free radical polymerizable group;

B is a supporting backbone;

$m \geq 1$; and $n \geq 2$.

39. The QHB-modified free radical polymerizable compound of claim 38 in which the QHB unit is selected from:

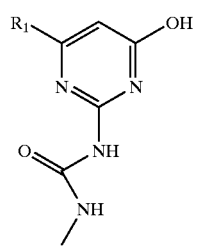

(I)

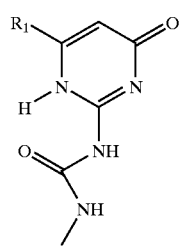

(II)

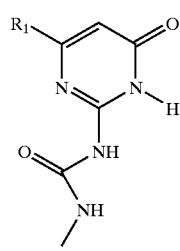

(III)

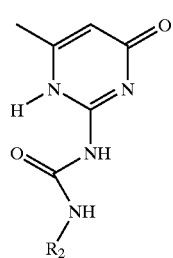

(IV)

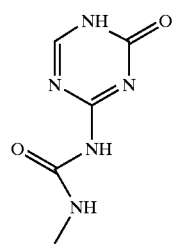

(V)

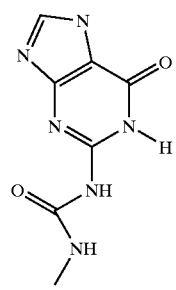

(VI)

in which $R_1$ is hydrogen or an alkyl group of 1 to 10 carbon atoms and $R_2$ is a residue from an isocyanate compound.

40. The QHB-modified free radical polymerizable compound of claim 39 in which the QHB unit is selected from structures I, II, and III, and $R_1$ is methyl.

41. The QHB-modified free radical polymerizable compound of claim 40 in which P comprises 1 to 5 free radical polymerizable groups.

42. The QHB-modified free radical polymerizable compound of claim 41 in which P comprises at least two free radical polymerizable groups, and the free radical polymerizable groups each comprise a $C=CH_2$ structural unit.

43. A free radical polymerizable composition comprising:

a free radical generating system; and a QHB-modified free radical polymerizable compound having the structure:

$(P)_m B(Q)_n$ in which:

Q is a moiety that comprises a QHB unit;

P is a moiety that comprises at least one free radical polymerizable group;

B is a supporting backbone;

$m \geq 1$; and $n \geq 2$.

44. The free radical polymerizable composition of claim 43 in which the QHB unit is selected from:

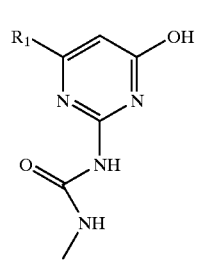

(I)

-continued

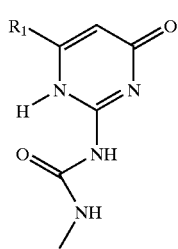
(II)

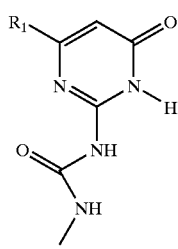
(III)

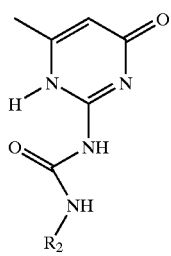
(IV)

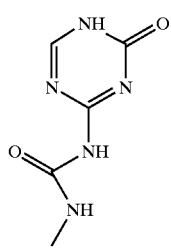
(V)

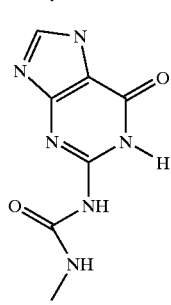
(VI)

in which R$_1$ is hydrogen or an alkyl group of 1 to 10 carbon atoms and R$_2$ is a residue from an isocyanate compound.

45. The free radical polymerizable composition of claim 44 in which the free radical polymerizable composition additionally comprises a photothermal conversion material.

46. The free radical polymerizable composition of claim 45 in which the QHB unit is selected from structures I, II, and III, and R$_1$ is methyl.

47. An imageable element comprising:
a substrate; and
a layer of a polymerizable composition over the substrate;
in which the polymerizable composition comprises:
a free radical generating system; and
a QHB-modified free radical polymerizable compound having the structure:

$$(P)_m B(Q)_n$$

in which:
Q is a moiety that comprises a QHB unit;
P is a moiety that comprises at least one free radical polymerizable group;
B is a supporting backbone;
m ≧ 1; and
n ≧ 2.

48. The imageable element of claim 47 in which the QHB unit is selected from:

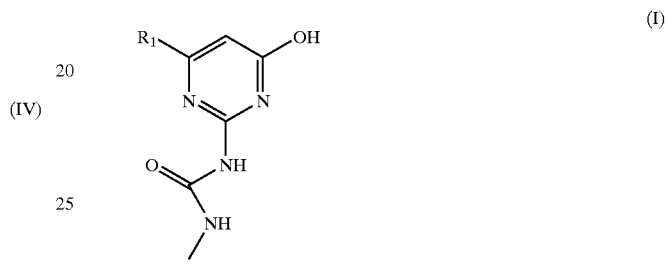
(I)

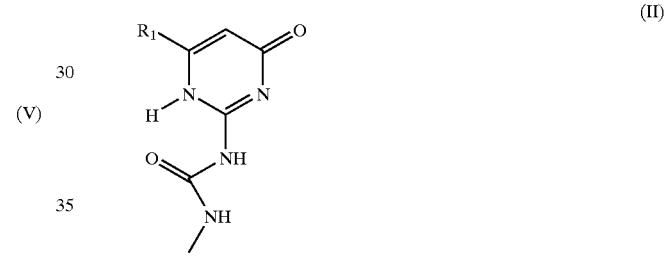
(II)

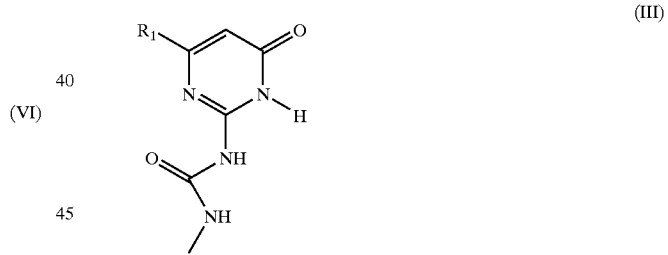
(III)

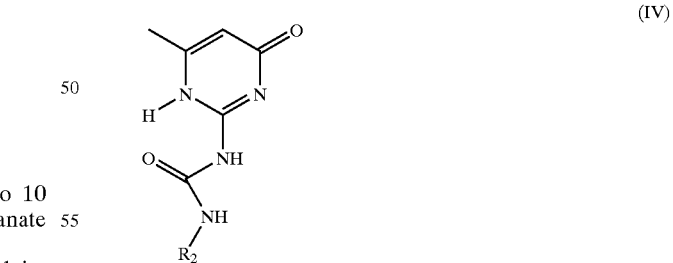
(IV)

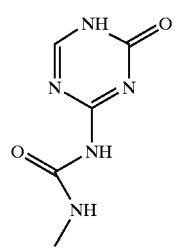
(V)

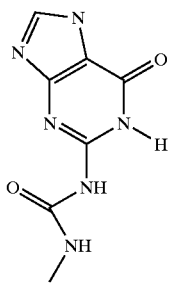

(VI)

in which $R_1$ is hydrogen or an alkyl group of 1 to 10 carbon atoms and $R_2$ is a residue from an isocyanate compound.

49. The imageable element of claim 48 in which the QHB unit is selected from structures I, II, and III, and $R_1$ is methyl.

50. The imageable element of claim 49 in which the free radical generating system comprises a polyhaloalkyl-substituted free radical producing compound; and a carboxylic acid is selected from the group consisting of N-phenyliminodiacetic acid; N-(carboxymethyl)-N-phenylglycine; and (3,4-dimethoxyphenylthio)acetic acid.

51. The imageable element of claim 49 in which the free radical polymerizable composition additionally comprises a photothermal conversion material.

52. The imageable element of claim 47 additionally comprising an underlayer between the substrate and the imageable layer.

53. A method for forming an image, the method comprising:
imaging an imageable element and forming an imaged imageable element comprising imaged regions and complementary unimaged regions; and
developing the imaged imageable element and removing the unexposed regions; p1 in which:
the imageable element comprises:
a substrate; and
a layer of a polymerizable composition over the substrate; the polymerizable composition comprising:
a free radical generating system; and
a QHB-modified free radical polymerizable compound having the structure:

in which:
Q is a moiety that comprises a QHB unit;
P is a moiety that comprises at least one free radical polymerizable group;
B is a supporting backbone;
$m \geq 1$; and
$n \geq 2$.

54. The method of claim 53 in which imaging is carried out with heat or infrared radiation.

55. The method of claim 53 in which imaging is carried out with ultraviolet laser or by exposure with ultraviolet radiation through a photomask.

56. A QHB-modified free radical polymerizable compound having the structure:

in which:
Q is a moiety that comprises a QHB unit;
P is a moiety that comprises at least one free radical polymerizable group;
B is a supporting backbone;
$m \geq 2$; and
$n \geq 1$.

57. The QHB-modified free radical polymerizable compound of claim 56 in which the QHB unit is selected from:

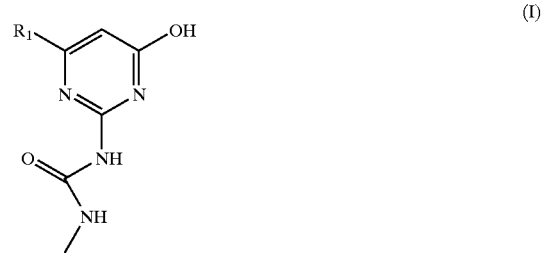

(I)

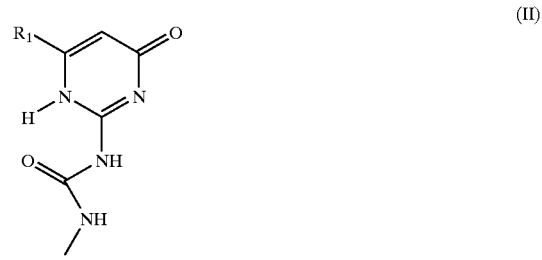

(II)

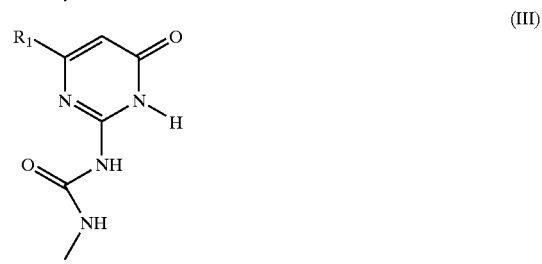

(III)

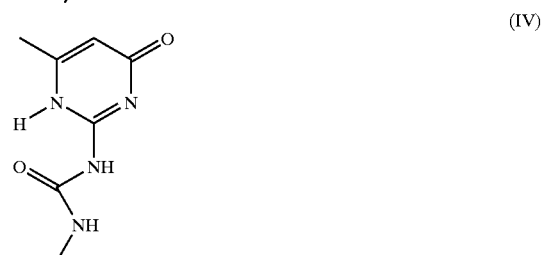

(IV)

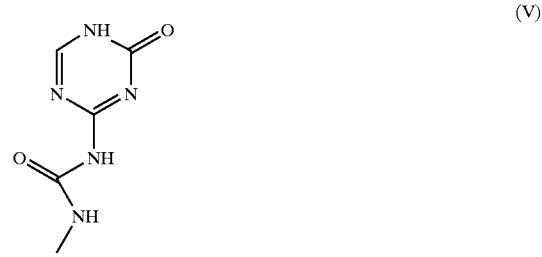

(V)

(VI)

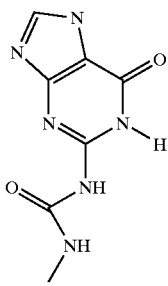

in which R₁ is hydrogen or an alkyl group of 1 to 10 carbon atoms and R₂ is a residue from an isocyanate compound.

58. The QHB-modified free radical polymerizable compound of claim 57 in which the QHB unit is selected from structures I, II, and III, and R₁ is methyl.

59. The QHB-modified free radical polymerizable compound of claim 58 in which n is at least 2, and P comprises 1 to 5 free radical polymerizable groups.

60. A free radical polymerizable composition comprising:

a free radical generating system; and a QHB-modified free radical polymerizable compound having the structure:

(P)ₘB(Q)ₙ in which:

Q is a moiety that comprises a QHB unit;

P is a moiety that comprises at least one free radical polymerizable group;

B is a supporting backbone;

m≧2; and n≧1.

61. The free radical polymerizable composition of claim 60 in which the QHB unit is selected from:

(I)

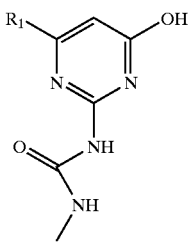

(II)

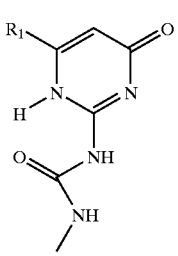

(III)

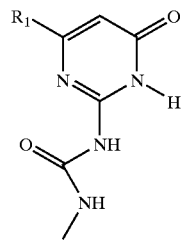

(IV)

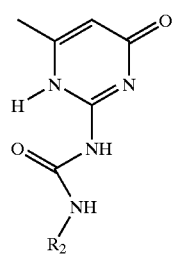

(V)

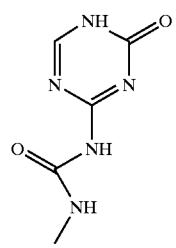

(VI)

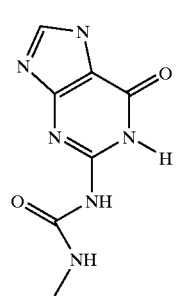

in which R₁ is hydrogen or an alkyl group of 1 to 10 carbon atoms and R₂ is a residue from an isocyanate compound.

62. The free radical polymerizable composition of claim 61 in which the free radical polymerizabie composition additionally comprises a photothermal conversion material.

63. The free radical polymerizable composition of claim 62 in which the QHB unit is selected from structures I, II, and III, and R₁ is methyl.

64. An imageable element comprising:

a substrate; and a layer of a polymerizable composition over the substrate;

in which the polymerizable composition comprises:

a free radical generating system; and a QHB-modified free radical polymerizable compound having the structure:

(P)ₘB(Q)ₙ in which:

Q is a moiety that comprises a QHB unit;

P is a moiety that comprises at least one free radical polymerizable group;

B is a supporting backbone;

m≧2; and n≧1.

65. The imageable element of claim 64 in which the QHB unit is selected from:

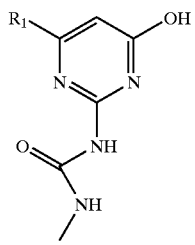

(I)

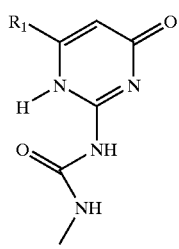

(II)

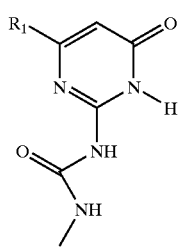

(III)

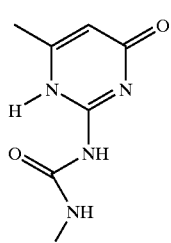

(IV)

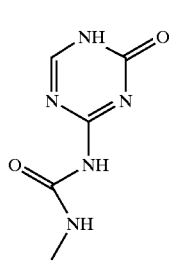

(V)

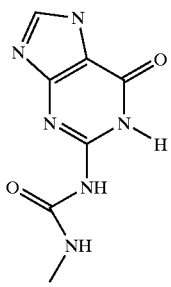

(VI)

in which $R_1$ is hydrogen or an alkyl group of 1 to 10 carbon atoms and $R_2$ is a residue from an isocyanate compound.

66. The imageable element of claim 65 in which the QHB unit is selected from structures I, II, and III, and $R_1$ is methyl.

67. The imageable element of claim 66 in which the free radical polymerizable composition additionally comprises a photothermal conversion material.

68. A method for forming an image, the method comprising:

imaging an imageable element and forming an imaged imageable element comprising imaged regions and complementary unimaged regions; and developing the imaged imageable element and removing the unexposed regions;

in which:

the imageable element comprises:

a substrate; and a layer of a polymerizable composition over the substrate; the polymerizable composition comprising:

a free radical generating system; and a QHB-modified free radical polymerizable compound having the structure:

$(P)_m B(Q)_n$ in which:

Q is a moiety that comprises a QHB unit;

P is a moiety that comprises at least one free radical polymerizable group;

B is a supporting backbone;

m≧2; and n≧1.

69. The method of claim 68 in which imaging is carried out with heat or infrared radiation.

70. The method of claim 68 in which imaging is carried out with ultraviolet laser or by exposure with ultraviolet radiation through a photomask.

* * * * *